United States Patent

Weissenfluh et al.

[11] Patent Number: 5,290,170
[45] Date of Patent: Mar. 1, 1994

[54] ABLATOR FOR USE IN DENTISTRY

[75] Inventors: Beat V. Weissenfluh, Gentilino; Bernhard Guggenheim; Ulrich Saxer, both of Zürich; Gianni Baffelli, Tesserete, all of Switzerland

[73] Assignee: Hawe-Neos Dental Dr. von Weissenfluh S.A., Gentilino, Switzerland

[21] Appl. No.: 824,362

[22] Filed: Jan. 23, 1992

[30] Foreign Application Priority Data

Jan. 23, 1991 [CH] Switzerland .................. 184/91

[51] Int. Cl.$^5$ ............... A61C 3/06; A61C 3/00; A61C 17/00
[52] U.S. Cl. .................. 433/142; 433/141; 433/143
[58] Field of Search .......... 433/141, 142, 143, 144, 433/148, 149

[56] References Cited

U.S. PATENT DOCUMENTS

| | | | |
|---|---|---|---|
| 3,660,902 | 5/1972 | Axelsson | 32/58 |
| 3,862,065 | 1/1975 | Yokokawa et al. | 260/185 |
| 4,780,083 | 10/1988 | Croll | 433/142 X |
| 4,795,344 | 1/1989 | Brewer, Jr. | 433/141 X |
| 4,919,616 | 4/1990 | Croll | 433/141 X |
| 5,118,291 | 6/1992 | Varaine | 433/141 X |

FOREIGN PATENT DOCUMENTS

| | | | |
|---|---|---|---|
| 0258566 | 7/1988 | Denmark | 433/142 |
| 0001013 | 3/1979 | European Pat. Off. . | |
| 0002904 | 7/1979 | European Pat. Off. | 433/141 |
| 0168059 | 1/1986 | European Pat. Off. . | |
| 0337443 | 10/1989 | European Pat. Off. . | |
| 0425357 | 5/1991 | European Pat. Off. . | |
| 106556 | 1/1898 | Fed. Rep. of Germany | 433/142 |
| 1-62152 | 3/1989 | Japan . | |

*Primary Examiner*—Gene Mancene
*Assistant Examiner*—Nicholas D. Lucchesi
*Attorney, Agent, or Firm*—Young & Thompson

[57] ABSTRACT

The ablator is made with synthetic resins reinforced so as to resist the mechanical stresses of flexion and abrasion. The resins are reinforced with metallic or non-metallic fibers totally incorporated in them, and are reinforced against wear due to abrasion by a modification in their surface molecular structure by means of a process of ionic implantation or similar procedures. Preferably, the synthetic resins used belong to the group of polyarylamides which exhibit better characteristics of mechanical resistance and of the duration of the sharpened edge of the ablator.

5 Claims, 1 Drawing Sheet

ABLATOR FOR USE IN DENTISTRY

FIELD OF THE INVENTION

The present invention has as its object an ablator for use in dentistry, characterized in that it is made of synthetic reinforced resins so as to resist the mechanical stresses of flexion and abrasion.

BACKGROUND OF THE INVENTION

The same applicant has already submitted a patent application on the same matter in which part of the concepts of the present application were already contained (Swiss patent application no. 184/91-6).

Present ablators, which are principally used to remove tartar, bacterial plaque and radicular cement, are manufactured of metal, usually steel.

SUMMARY OF THE INVENTION

The use of these metal instruments very often involves an excessive removal of healthy tooth matter, which can cause hypersensitivity of the dentine.

This is avoided by making, according to the invention, the ablator of synthetic resins, properly reinforced so as to prevent breakage. In a preferred embodiment, this result is obtained by inserting reinforcement fibers into the ablator.

These fibers can, for example, be made of glass, carbon or even metal, and they are, in any case, completely incorporated into the synthetic resin forming the ablator. A preferred embodiment provides that the fibers be essentially parallel to the longitudinal axis of the ablator.

In another embodiment, the ablator is subsequently reinforced against wear by a modification in the surface molecular structure of the synthetic resins by means of a process of ionic implantation or of other coating processes having similar effects.

BRIEF DESCRIPTION OF THE DRAWING

The attached drawings represent a non-limiting preferred embodiment of the ablator that is the object of the invention.

DETAILED DESCRIPTION OF THE INVENTION

Figures 1, 2:
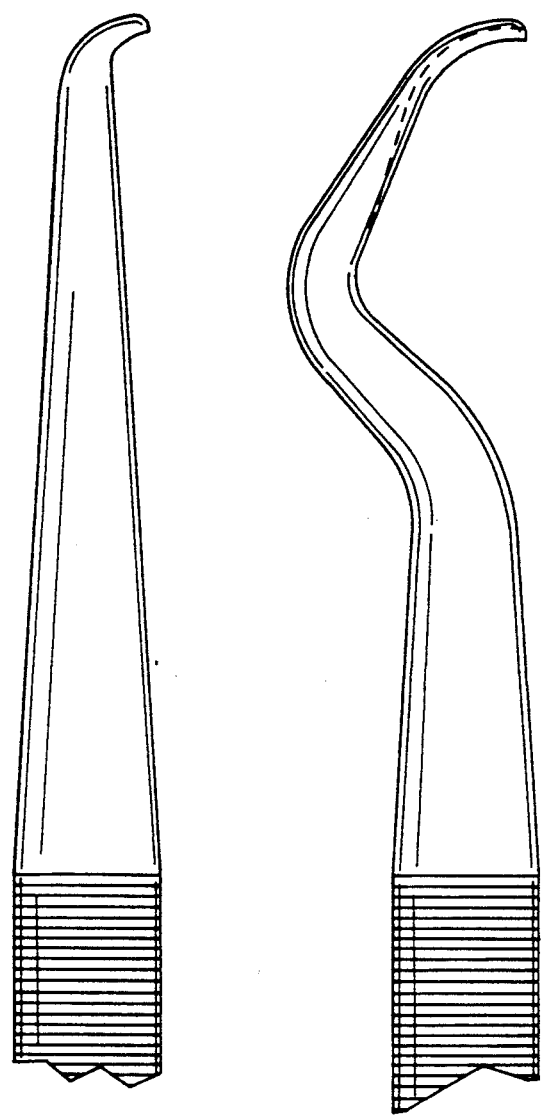
FIG. 1 represents it in lateral view.
FIG. 2 represents it in lateral view and rotated 90° with respect to FIG. 1.
Figure 3:
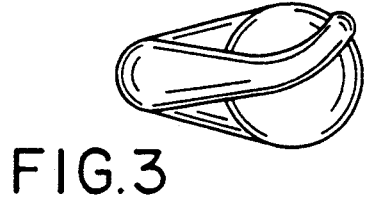
FIG. 3 represents it in front view.

The ablator can also be made of thermoplastic synthetic resins like nylon, polyamide resins and the like, but a preferred embodiment provides the use of synthetic resins belonging to the group of polyarylamides.

These latter have a relatively high modulus of elasticity ($>15,000$ N/mm$^2$) with respect to that of other resins commonly used (ca. $4+5,000$ N/mm$^2$), moreover they are endowed with extreme fluidity in the liquid state, so that the ablators obtained with their use already exhibit the final sharpening of the cutting edge at the end of the thermoplastic stamping itself without the need for repeated operations. Moreover they prove to be easily resharpened.

A subsequently improved result as to the resistance to wear due to abrasion is obtained by modifying the surface molecular structure of the ablator made from polyarylamides by a process of ionic implantation or other processes of coating having similar effects.

In this way, the endurance of the sharpened edge is prolonged, while at the same time the ablator's resistance to wear is increased.

By means of the several disclosed embodiments, the characteristics of resistance to flexion and abrasion can be modified. Similarly, the resistance characteristics of the sharpened edge, as well as the possibility of resharpening the ablator can also be modified.

This also involves a possibility of adapting the instrument itself to the type of procedure and to the context in which the procedure itself is done.

For example, the above mentioned characteristics can be adapted in various manners depending on whether work is being done on radicular cement, on an implant, or on delicate metal components such as pins.

The shape of the ablator and the nature of the materials used can vary in any case, while remaining within the scope of protection of the patent conferred by the attached claims.

We claim:

1. An ablator for use in dentistry, having a generally longitudinal axis and a handle at one end and an ablator tip at the other end, and made of synthetic resin reinforced by fibers to resist mechanical stresses, said synthetic resin belonging to the group of polyamides, said fibers consisting of carbon fibers and being totally incorporated within the polyamide resin and being arranged substantially parallel to the longitudinal axis of the ablator.

2. The ablator according to claim 1, wherein the polyamide resin belongs to the group of polyarylamides.

3. The ablator according to claim 2, wherein the ablator is further reinforced against wear due to abrasion by means of a process of ionic implantation that modifies the superficial molecular structure of the synthetic resin.

4. The ablator according to claim 1, wherein the ablator is further reinforced against wear due to abrasion by means of a process of ionic implantation that modifies the superficial molecular structure of the synthetic resin.

5. The ablator according to claim 1, wherein the synthetic resin has a modulus of elasticity greater than 15,000 N/mm$^2$.

* * * * *

UNITED STATES PATENT AND TRADEMARK OFFICE
CERTIFICATE OF CORRECTION

PATENT NO. : 5,290,170
DATED : March 1, 1994
INVENTOR(S) : Beat VON WEISSENFLUH et al.

It is certified that error appears in the above—identified patent and that said Letters Patent is hereby corrected as shown below:

On the title page, in Item [19], change the surname of the inventor from "Weissenfluh" to --Von Weissenfluh--.

On the title page, in Item [75] Inventors, change the first inventor's name from "Beat V. Weissenfluh" to --Beat Von Weissenfluh--.

Signed and Sealed this

Twenty-first Day of March, 1995

Attest:

BRUCE LEHMAN

*Attesting Officer*     *Commissioner of Patents and Trademarks*